United States Patent
Park et al.

(10) Patent No.: US 9,254,088 B2
(45) Date of Patent: Feb. 9, 2016

(54) HEADSET DEVICE AND METHOD MEASURING A BIOSIGNAL

(75) Inventors: Kun Kook Park, Yongin-si (KR); Jin Sang Hwang, Yongin-si (KR); Kun Soo Shin, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 2355 days.

(21) Appl. No.: 11/785,233

(22) Filed: Apr. 16, 2007

(65) Prior Publication Data
US 2008/0013777 A1    Jan. 17, 2008

(30) Foreign Application Priority Data
Apr. 20, 2006    (KR) .................. 10-2006-0035874

(51) Int. Cl.
*A61B 5/05* (2006.01)
*A61B 5/00* (2006.01)
*H04R 5/033* (2006.01)

(52) U.S. Cl.
CPC ............. *A61B 5/0059* (2013.01); *A61B 5/6803* (2013.01); *A61B 5/6814* (2013.01); *A61B 5/6887* (2013.01); *A61B 2562/0219* (2013.01); *H04R 5/033* (2013.01)

(58) Field of Classification Search
USPC .......... 381/370, 374, 376, 381, 384; 600/309, 600/310, 407, 473
See application file for complete search history.

(56) References Cited

U.S. PATENT DOCUMENTS

| | | | |
|---|---|---|---|
| 2,734,484 A * | 2/1956 | O'Sullivan .................. 401/113 |
| 4,301,808 A * | 11/1981 | Taus .............................. 600/500 |
| 4,709,702 A * | 12/1987 | Sherwin ........................ 600/383 |
| 5,273,037 A * | 12/1993 | Itil et al. ....................... 600/383 |
| 5,487,609 A * | 1/1996 | Asada ............................ 384/18 |
| 5,740,812 A * | 4/1998 | Cowan ......................... 600/545 |
| 2003/0018274 A1 * | 1/2003 | Takahashi et al. ........... 600/500 |
| 2004/0106856 A1 * | 6/2004 | Kimura ........................ 600/310 |
| 2005/0124463 A1 * | 6/2005 | Yeo et al. ......................... 482/8 |

* cited by examiner

*Primary Examiner* — Tse Chen
*Assistant Examiner* — Jason Ip
(74) *Attorney, Agent, or Firm* — Harness, Dickey & Pierce

(57) ABSTRACT

A headset device includes a headset body, a connection unit to move relative to the headset body, and a sensor unit having a light emitting element and a light receiving element to sense a biosignal, the sensor unit mounted to the connection unit to make contact with a human body. The sensor unit may measure a biosignal of a user, and the headset body and the sensor unit are indirectly connected by the connection unit. Accordingly, the sensor unit may be isolated from movement or vibration received through the headset body.

14 Claims, 9 Drawing Sheets

HEADSET DEVICE AND METHOD MEASURING A BIOSIGNAL

CROSS-REFERENCE TO RELATED APPLICATIONS

This application claims the benefit of Korean Patent Application No. 10-2006-0035874, filed on Apr. 20, 2006, in the Korean Intellectual Property Office, the disclosure of which is incorporated herein by reference.

BACKGROUND

1. Field

One or more embodiments of the present invention relate to a headset device, and more particularly, to a headset device and a method measuring a biosignal while a user is working out.

2. Description of the Related Art

Various types of sensors are used in order to measure biosignals such as an electrocardiogram or pulse. For example, an electrode sensor may be used for sensing a change of a current, or photo plethysmography (PPG) may be used for sensing a change of light. Such sensors may be installed in articles of clothing such as gloves, hats, and accessories. Sensors may allow the measurement in real time of a change in the physical condition of a user who is wearing the clothing. For example, a headset device including an earphone or headphones may be used to measure a change in the physical condition of a user who is exercising. A headset device is any device that may be placed on the head of a user, and may be used for easy measurement of a biosignal. Also, a headset device may provide music while measuring the biosignal. Accordingly, measurements may be performed with minimal interference to the user and an application range may be relatively broad.

In order to improve the sensitivity of a sensor and obtain reliable results, a user whose biosignal is being measured should remain relatively still. When the user is moving or exercising, any biosignal measured may be inaccurate. The inaccuracy may result from the movement of the sensor with respect to the user's body that results from jarring and movement during exercise. In addition, the change may be unpredictably irregular. Particularly, since the head is an area having a wide range of movement, any measurement made in the head area may be highly distorted during exercise.

Any distortion caused by user movement may vary depending on the direction of the movement in relation to a human body. As an example, a headset device may be more highly influenced by a movement in a perpendicular direction than a movement in a length-wise direction. The length-wise direction may indicate a direction parallel to the surface of the skin making contact with the sensor. The perpendicular, or transverse, direction may indicate a direction perpendicular to the surface of the skin making contact with the sensor, i.e. perpendicular to the length-wise direction.

SUMMARY

An aspect of the present invention provides a headset device and a method measuring a biosignal using the headset device that is capable of offsetting movements of a user, for example during exercise.

An aspect of the present invention also provides a headset device that has various configurations and a method measuring a biosignal using the headset device, which may efficiently cope with user movements.

Additional aspects, features, and/or advantages of the present invention will be set forth in part in the description which follows and, in part, will be apparent from the description, or may be learned by practice of the invention.

According to an aspect of the present invention, a headset device includes a headset body and a sensor unit. Also, a connection unit indirectly connecting the headset body and the sensor unit is included. In this instance, the connection unit may prevent a movement of the headset body from being directly transferred to the sensor unit. Various configurations may be used for the connection unit, and the sensor unit may use a variety of contact or contactless sensors as well as a reflective photosensor.

According to another aspect of the present invention, a connection unit moves relative to the headset body. In this instance, the connection unit may use features such as two-dimensional rotation, three-dimensional rotation, sliding, and bending. Also, since the connection unit mostly induces a transverse movement, the connection unit may offset differences of a movement speed, a movement distance, or a movement direction between a head and a headset body when a user is working out. As mentioned above, the transverse direction may indicate a vertical direction to an axis connecting the headset body and the sensor unit.

A joint combined with the headset body may be used as the connection unit. Also, a spring element, ends of which are separately supported by the headset body and the sensor unit respectively, may be used as the connection unit. Depending on circumstances, a ball or a roller joint combined with the headset body and the sensor unit is provided, thereby preventing a movement of the headset device from being transferred to the sensor unit.

A photosensor using light may be used as sensor unit. Depending on the circumstances, a light emitting element and a light receiving element may be arranged to face each other on both sides of an object. However, having the light emitting element and the light receiving element face in one direction and measuring a reflected light may also be effective.

According to an aspect of the present invention, a connection unit may include a first connecting part fixed to the headset body, and a second connecting part rotatably engaged with an end of the first connecting part. In this instance, the sensor unit is mounted to an end of the second connecting part, and may rotate two-dimensionally or three-dimensionally.

According to another aspect of the present invention, a connection unit may include a sensor receiving part that is integrally connected with the headset body, and a spring element installed in the sensor receiving part. The sensor unit is elastically supported by the spring element, and may offset a change with respect to a transverse movement of the sensor unit as well as a longitudinal movement of the sensor unit.

According to another aspect of the present invention, a connection unit may include a first receiving part fixed to the headset body, a second receiving part engaged with the first receiving part to slide relative to the first receiving part, and at least one bearing which maintains a rolling contact between the first and second receiving part.

According to another aspect of the present invention, there is provided a method measuring a biosignal by wearing a headset device including a headset body, and a sensor unit installed in the headset body, whereby the sensor unit is closely attached to a target portion of a body, the method including offsetting a movement transferred from the headset body to the sensor unit using a connection unit interposed between the headset body and the sensor unit and monitoring a biosignal of the body obtained by the sensor unit.

According to another aspect of the present invention, a measurement device for measuring a biosignal may be configured using a material wearable on a human body. The biosignal measurement device includes a body wearable on a human body, a connection unit to move relative to the body, and a sensor unit mounted to the connection unit, to make contact with a portion of a human body. The connection unit may restrict a movement of the sensor unit to move substantially perpendicular to an imaginary line between the headset body and the sensor unit. A wearable article such as a pair of glass, a belt, a glove as well as a headset may also be used.

BRIEF DESCRIPTION OF THE DRAWINGS

These and/or other aspects, features, and advantages of the present invention will become apparent and more readily appreciated from the following detailed description, taken in conjunction with the accompanying drawings of which.

DETAILED DESCRIPTION OF EMBODIMENTS

Figure 1:
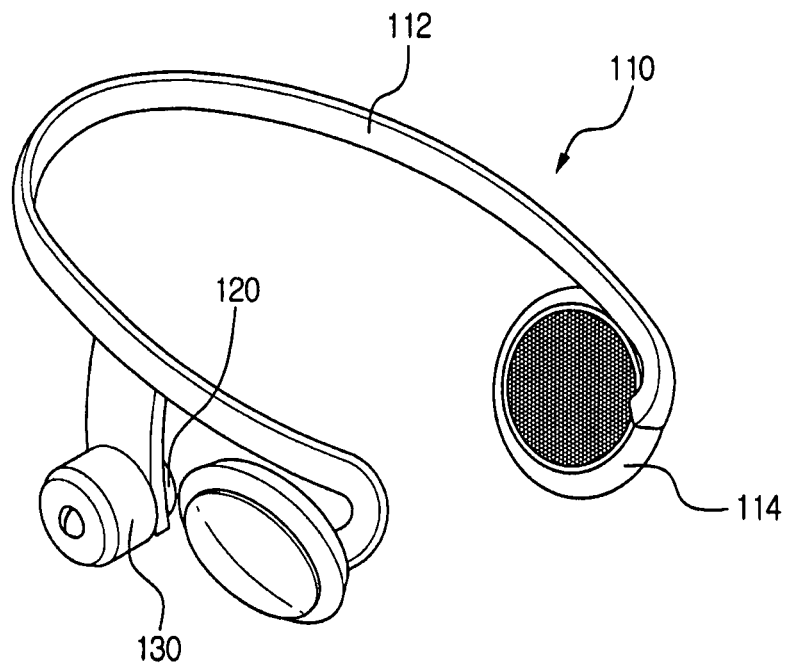
FIG. 1 illustrates a headset device, according to one or more embodiments of the present invention.

Reference will now be made in detail to one or more embodiments of the present invention, examples of which are illustrated in the accompanying drawings, wherein like reference numerals refer to the like elements throughout. Embodiments are described below in order to explain the present invention by referring to the figures.

Figure 2:
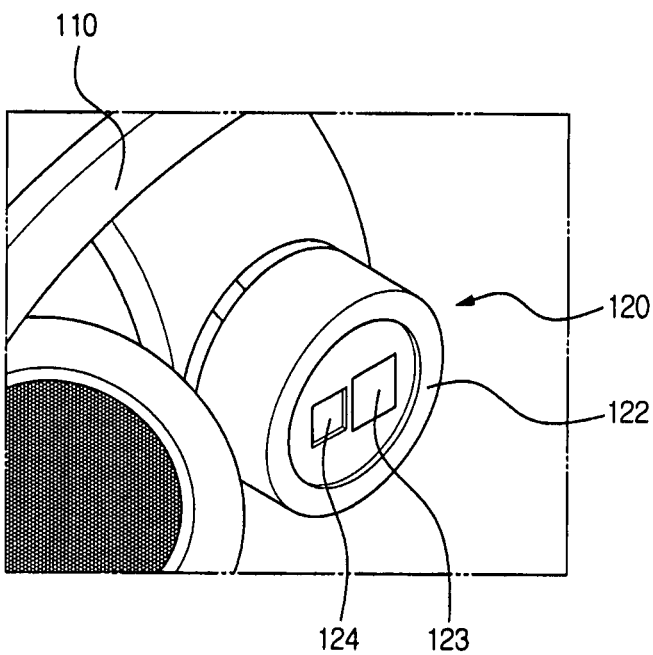
FIG. 2 illustrates a sensor unit of the headset device in FIG. 1, according to one or more embodiments of the present invention.

FIG. 1 illustrates a headset device according to one or more embodiments of the present invention. FIG. 2 illustrates a sensor unit of a headset, such as that in FIG. 1. Further, FIG. 3 illustrates a cross-section of a connection unit and a sensor unit, the headset device in FIG. 1.

Figure 3:
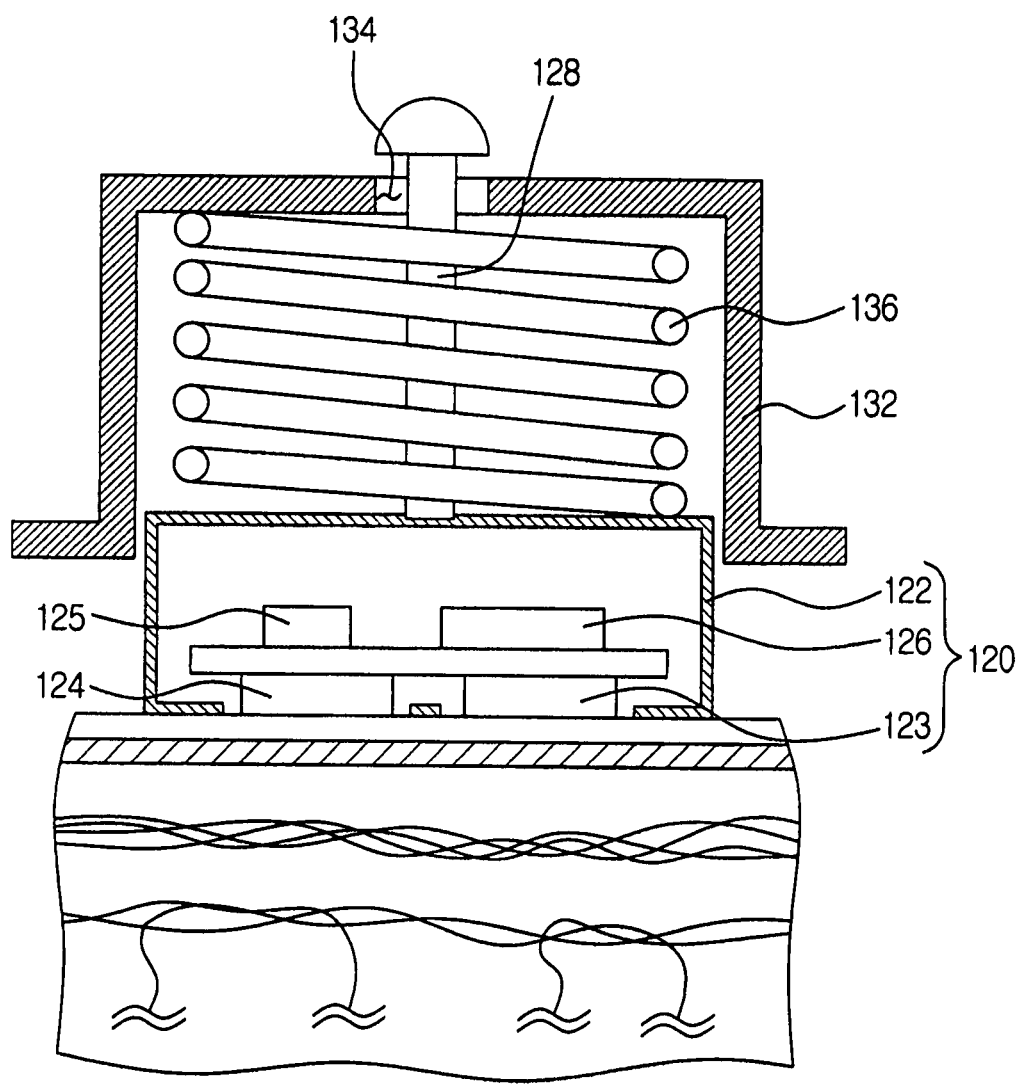
FIG. 3 illustrates a cross-section of a connection unit and a sensor unit, such as with the headset device in FIG. 1, according to one or more embodiments of the present invention.

Referring to FIGS. 1 through 3, a headset device 100 may include a headset body 110, a sensor unit 120, and a connection unit 130, for example. The connection unit 130 may enable the headset body 110 and the sensor unit 120 to move relative to each other using a spring, for example. The connection unit 130 may limit movement of the sensor unit 120 with respect to the surface of the skin, decreasing distortion caused by such movement.

The headset body 110 may include a generally arch-shaped head holder 112, with a speaker or speakers 114 installed on one end or both ends of the head holder 112 to transfer audio content. The head holder 112 shape may include, without limitation, a typical headset passing over the top of the head, a rear band headset passing around the back of the head, or a headset slipping around one or both external ears.

The sensor unit 120 may include a sensor housing 122. A printed circuit board including a light emitting element 123, a light receiving element 124, an amplifier 125, and an acceleration sensor 126 may be provided in the sensor housing 122, for example. One side of the sensor housing 122 makes contact with a human body. In addition, the sensor housing 122 may generate light through a contact side, and may receive a reflected light with the light-receiving element 124. Various biosignals including a pulse may, thus, be measured using the light emitting element 123 and the light receiving element 124. The biosignals sensed by the light receiving element 124 may further be amplified with the amplifier 125. Measured biosignals may be converted into a digital format and may be stored in an internal storage medium or an external server. An acceleration, transmitted to the sensor unit 120, may be measured by the acceleration sensor 126. In addition, a measured biosignal value may be corrected by a measured acceleration.

The connection unit 130 may enable the headset body 110 and the sensor unit 120 to move relative to each other. In the present embodiment, the connection unit 130 may include a sensor receiving part 132 and a spring 136, for example. A first end of the spring 136 may be connected with an inner surface of the sensor receiving part 132. A second end of the spring 136 may be connected with a top surface of the sensor housing 122. The sensor unit 120 may move with respect to the headset body 110, as shown in FIG. 3. More specifically, the sensor unit 120 may move along an axis substantially perpendicular to the surface of a user's head, due to elongation or compression of the spring 136. The sensor unit 120 may also maintain an original position without an external force, since the spring 136 provides dynamic stability along its axis of compression, and remains in contact with the skin, even during periods of exercise or great activity.

As illustrated in FIG. 3, the sensor receiving part 132 may include the spring 136. An end of the spring 136 may elastically support the sensor housing 122. Here, a guide bar 128, which may pass through the spring 136, may be provided on a top surface of the sensor housing 122. The guide bar 128 may be connected with an end of the sensor receiving part 132, and an end of the guide bar 128 may pass through a hole 134 in the end of the sensor receiving part 132. The hole 134 of the sensor receiving part 132 may have a diameter through which the guide bar 128 may rotate on the basis of a top surface of the guide bar 128. Thus, for example, the sensor unit 120 may absorb forces along an axis substantially perpendicular to the surface of a user's head.

The end of the guide bar 128 may be passed through the hole 134 of the sensor receiving part 132, to prevent the sensor unit 120 from separating from the sensor receiving part 132 by the spring 136, for example.

When a user is working out, most displacements between the headset body 110 and the sensor unit 120 occur widthwise, or parallel to the surface of the skin. Also, a widthwise movement in the headset device may not greatly affect measurement. The spring 136, may absorb forces along an axis substantially perpendicular to the surface of a user's head, inside the sensor receiving unit 132. Accordingly, the sensor unit 120 may make stable contact with a human body regardless of a perpendicular movement of the headset body 110. Here, the sensor unit 120 need not make excessive contact with the human body. Accordingly, the headset device may be comfortable, and a user may wear the headset device for a long time.

Figure 4:
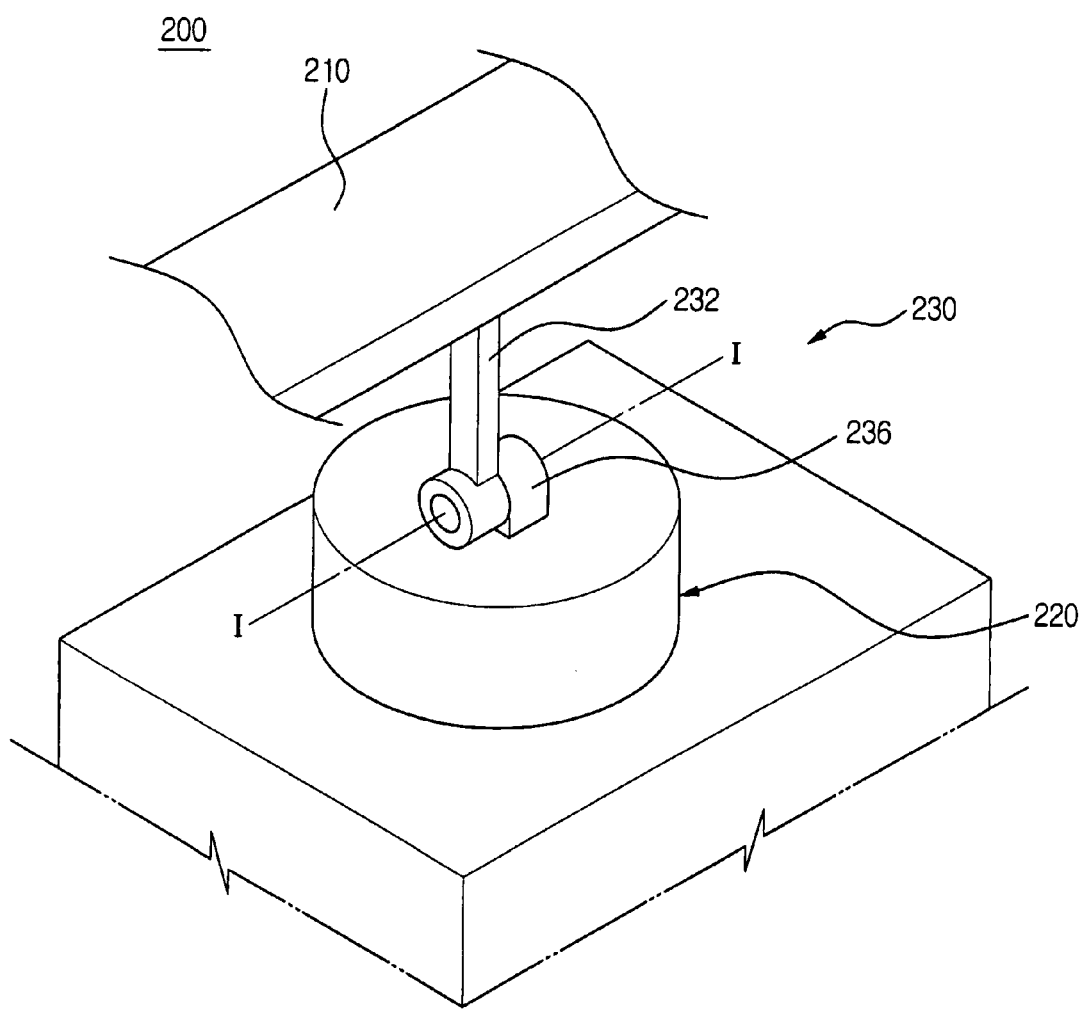
FIG. 4 illustrates a headset device according to one or more embodiments of the present invention.
Figure 5:
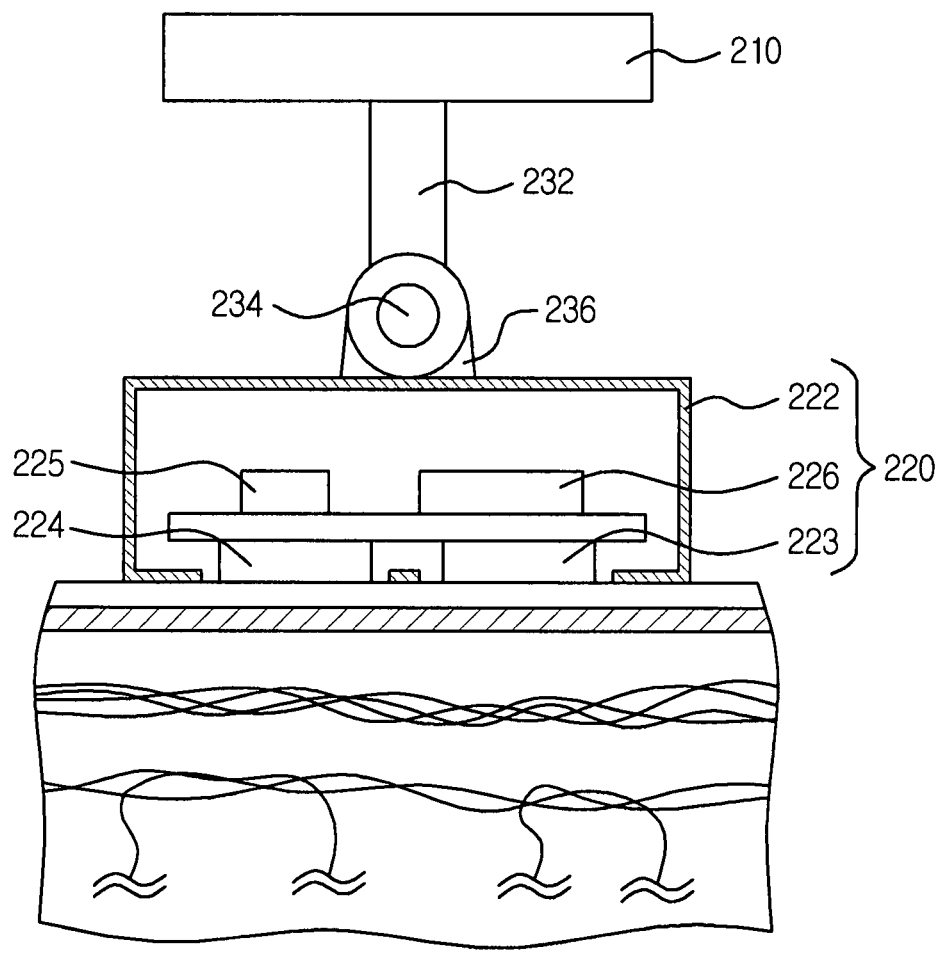
FIG. 5 illustrates a cross-section of a connection unit and a sensor unit, such as with the headset device in FIG. 4, according to one or more embodiments of the present invention.

FIG. 4 illustrates a headset device according to another one or more embodiments of the present invention. FIG. 5 illustrates a cross-section of a connection unit and a sensor unit, such as with the headset device in FIG. 4.

Referring to FIGS. 4 and 5, a headset device 200 may include a headset body 210, a sensor unit 220, and a connection unit 230, for example. The connection unit 230 may enable the headset body 210 and the sensor unit 220 to move relative to each other using a general hinge, for example. In addition, the connection unit 230 may move within a greater range for a transverse movement than for a longitudinal movement.

The headset body 210 may include a generally arch-shaped head holder 112. A speaker or speakers may be installed on one end or both ends of the head holder to transfer audio content. The head holder shape may include, without limitation, a typical headset passing over the top of the head, a rear band headset passing around the back of the head, or a headset slipping around one or both external ears.

The sensor unit 220 may include a sensor housing 222. A printed circuit board including a light emitting element 223, a light receiving element 224, an amplifier 225, and an acceleration sensor 226 may be provided in the sensor housing 222, for example. One side of the sensor housing 222 makes contact with a human body. Here, the sensor housing 222 may generate light on a contacted side, and may receive a reflected light through the light-receiving element 224. Various biosignals including a pulse may be measured using the light emitting element 223 and the light receiving element 224, and biosignals sensed by the light receiving element 224 may be amplified with the amplifier 225. Measured biosignals may be converted into a digital format and may be stored in an internal storage medium or an external server. An acceleration, transmitted to the sensor unit 220, may be measured by the acceleration sensor 226. Here, a measured biosignal value may be corrected by a measured acceleration.

In the present embodiment, a photosensor including a light emitting element and a light receiving element is used. However, an effect of the present invention may also be achieved using a sensor component sensitive to movement.

Referring again to FIGS. 4 and 5, the connection unit 230 enables the headset body 210 and the sensor unit 220 to move relative to each other. Here, the sensor unit 230 may rotate on an axis I, defined by a hinge, such that when the sensor unit 220 is rotating while making contact with a human body, the sensor unit 220 moves substantially widthwise. Accordingly, the rotating may be considered as widthwise movement.

In the present embodiment, the connection unit 230 may include a first connecting part 232 fixed to the headset body 210, and a second connecting part 236 fixed to the sensor housing 222, and rotatably engaged with an end of the first connecting part 232, for example. The first connecting part 232 and the second connecting part 236 may be rotatably connected by a two-dimensional hinge. The sensor unit 220 may move substantially perpendicular to an imaginary line between the headset body and the sensor unit, such that the sensor unit 220 may continue to make stable contact with a human body through a rotation of the hinge 234 corresponding to a movement of the headset body 210. The hinge 234, may include a torsion spring, for example, to enable the sensor unit 220 to automatically maintain a fixed position.

When a user is working out, most displacements between the headset body 210 and the sensor unit 220 occur widthwise. Also, a movement of a longitudinal component in the headset device may not greatly affect a measurement. Although there is no longitudinal movement of the sensor unit, a satisfactory measurement may still be obtained.

Figure 6:
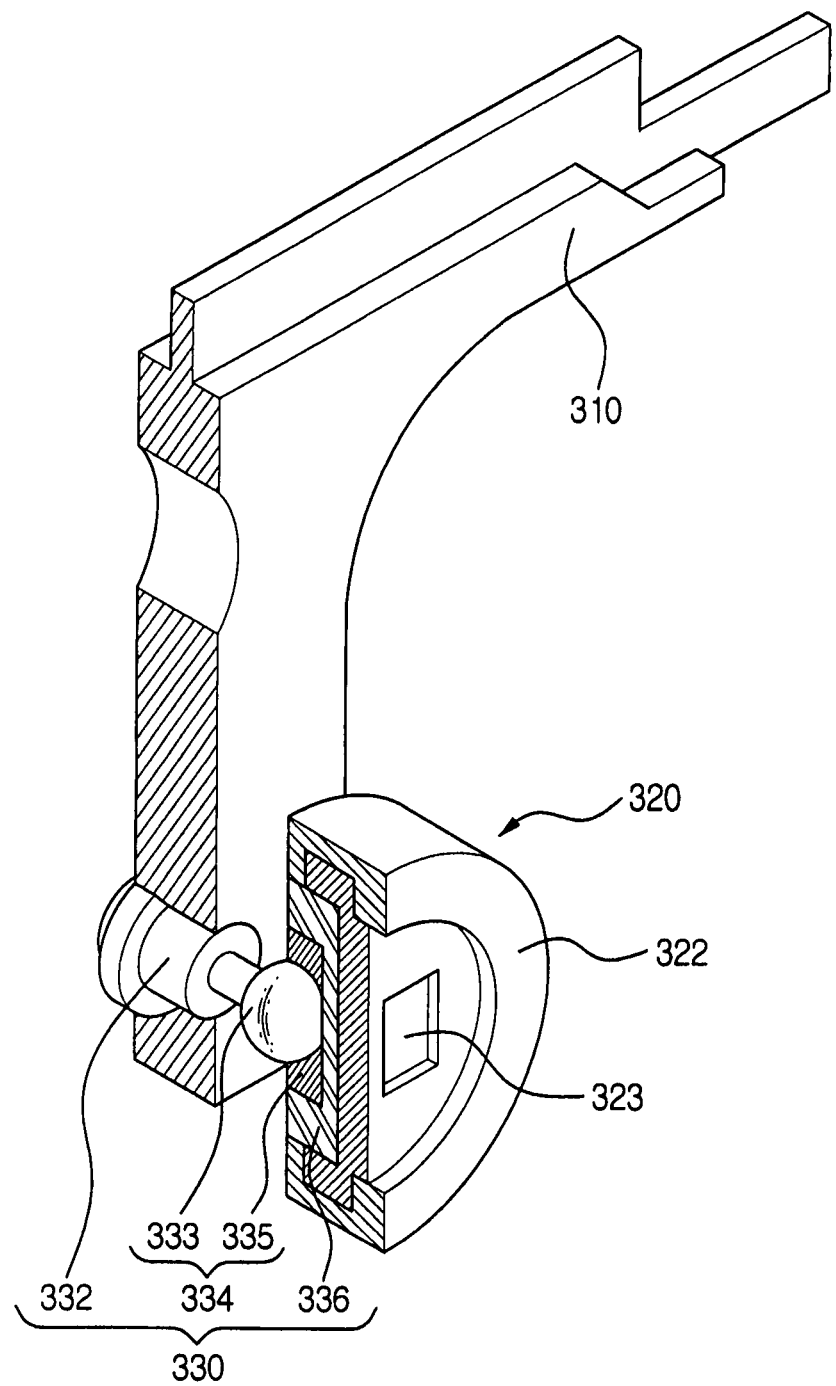
FIG. 6 illustrates a cross-section of a headset device according to one or more embodiments of the present invention.
Figure 7:
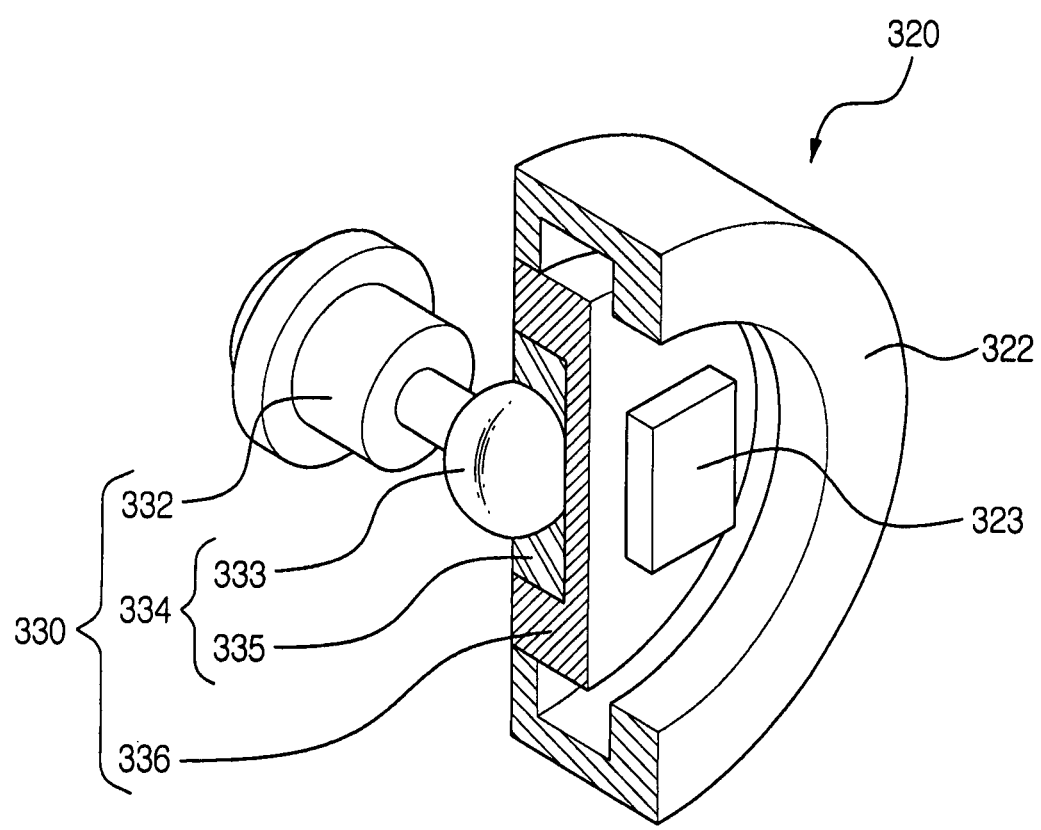
FIG. 7 illustrates a cross-section of a connection unit and a sensor unit, such as with the headset device in FIG. 6, according to one or more embodiments of the present invention.

FIG. 6 illustrates a cross-section of a headset device according to another embodiment of the present invention. FIG. 7 further illustrates a cross-section of a connection unit and a sensor unit of the headset device, such as that with FIG. 6.

Referring to FIGS. 6 and 7, a headset device may include a headset body 310, a sensor unit 320 and a connection unit 330, for example. The connection unit 330 may enable the headset body 310 and the sensor unit 320 to move relative to each other using a ball joint, for example. Also, the connection unit 330 may allow transverse movements rather than longitudinal movements. Above was described a sensor unit 220 that may rotate on one axis in a headset device 200, as illustrated in FIGS. 4 and 5. However, in the present embodiment, the sensor unit 320 may rotate on a plurality of axes in the headset device 300.

The headset body 310 may include a generally arch-shaped head holder 112. A speaker or speakers may be installed on one end or both ends of the head holder to transfer audio content. The head holder 112 shape may include, without limitation, a typical headset passing over the top of the head, a rear band headset passing around the back of the head, or a headset slipping around one or both external ears. Alternate embodiments are equally available.

The sensor unit 320 may include a sensor housing 322, for example. A printed circuit board including a light emitting element 323, a light receiving element, which is not shown, an amplifier, a wire/wireless transceiving unit, and an acceleration sensor may be provided in the sensor housing 322, for example. One side of the sensor housing 322 makes contact with a human body. Also, the sensor housing 322 may generate light on a contacted side, and may receive a reflected light through the light-receiving element. Various biosignals including a pulse may be measured using the light emitting element 323 and the light receiving element, and the biosignals sensed by the light receiving element may be amplified through the amplifier. Measured biosignals may be converted into a digital format and may be stored in an internal storage medium or an external server. Depending on circumstances, an acceleration transmitted to the sensor unit may be measured by the acceleration sensor. Here, a measured biosignal value may be corrected by a measured acceleration.

The connection unit 330 enables the headset body 310 and the sensor unit 320 to move relative to each other. The connection unit 330 may three-dimensionally rotate, because the connection unit 330 is connected using a ball joint in this example. When the sensor unit 320 is rotating to make contact with a human body, the sensor unit 320 moves substantially widthwise. Accordingly, the rotating may be considered as moving widthwise.

In the present embodiment, the connection unit 330 may include a first connecting part 332 fixed to the headset body 310, a second connecting part 336 fixed to the sensor housing 322 and rotatably engaged with an end of the first connecting part 332, for example. A ball 333 may be formed on an end of the first connecting part 332, a ball receiving part 335 may be formed on an end of the second connecting part 336. Accordingly, a ball joint 334 may be constructed. The second connecting part 336 may three-dimensionally rotate by a rotation of the ball joint 334, such that the sensor unit 320 may stably make contact with a human body by suitably varying an angle of a contact side based on a shape of the human body.

The sensor unit 320 may rotate back and forth as well as right and left on the basis of the headset body 310. The sensor unit 320 may stably continue to make contact with a human body through a free rotation of the ball joint 334 corresponding to a movement of the headset body 310.

When a user is working out, most displacements between the headset body 310 and the sensor unit 320 occur widthwise. A movement of a longitudinal component in the headset device may not greatly affect a measurement. Although there is no longitudinal movement, a satisfactory measurement may be obtained.

Figure 8:
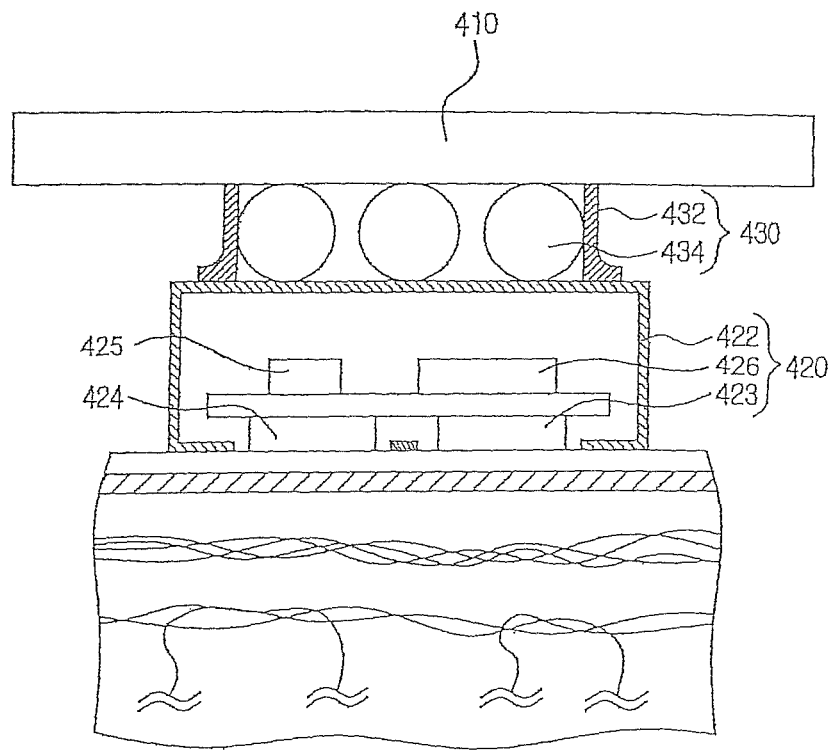
FIG. 8 illustrates a cross-section of a connection unit and a sensor unit, such as with the headset device according to one or more embodiments of the present invention.

FIG. 8 illustrates a front cross-section of a connection unit and a sensor unit of the headset device according to still another embodiment of the present invention. Further, FIG. 9 illustrates a side cross-section of a connection unit and a sensor unit, such as with the headset device in FIG. 8.

Figure 9:
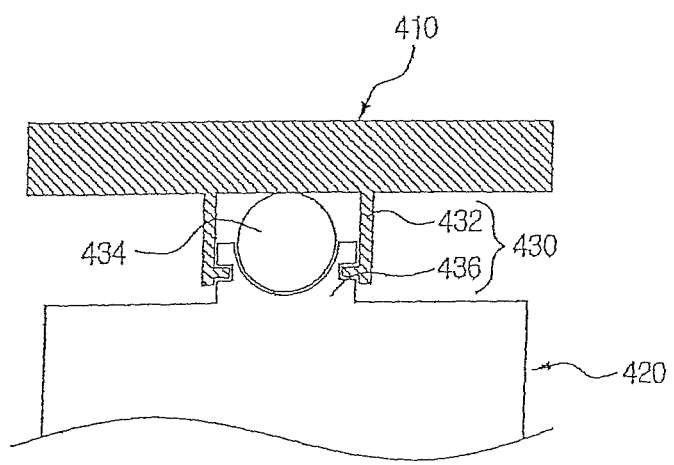
FIG. 9 illustrates another cross-section of a connection unit and a sensor unit, such as with the headset device in FIG. 8, according to one or more embodiments of the present invention.

Referring to FIGS. 8 and 9, a headset device may include a headset body 410, a sensor unit 420, and a connection unit 430, for example. The connection unit 430 may enable the headset body 410 and the sensor unit 420 to move relative to each other using a bearing. Here, the connection unit 430 may move within a greater range for a transverse movement than for a longitudinal movement. In this instance, the headset device 400 illustrated in FIGS. 8 and 9 may slide using the bearing. However, the headset device 400 may move widthwise using various configurations such as a guide projection, a guide groove, a guide bar, and a guide rail.

The headset body 410 may include a head holder in a shape of an arch. In this instance, a speaker or speakers may be installed on one end or both ends of the head holder to transfer audio content. The head holder is in a shape of a general headset passing over a top of a head. Here, a rear band headset, passing around a back of a head, and the like may be used.

The sensor unit 420 includes a sensor housing 422, with a printed circuit board including a light emitting element 423, a light receiving element 424, an amplifier 425, a wired/wireless transceiving unit, and an acceleration sensor 426 provided in the sensor housing 422, for example. One side of the sensor housing 422 makes contact with a human body. Further, the sensor housing 422 may generate light on a contacted side, and may receive a reflected light through the light-receiving element 424. Various biosignals including a pulse may be measured using the light emitting element 423 and the light receiving element 424, such that the biosignals sensed by the light receiving element 424 may be amplified through the amplifier to be processed. Measured biosignals may be converted into a digital format and may be stored in an internal storage medium or an external server. An acceleration transmitted to the sensor unit 420 may be measured by the acceleration sensor. Thus, a measured biosignal value may be corrected by a measured acceleration.

The connection unit 430 may enable the headset body 410 and the sensor unit 420 to move relative to each other. For example, the sensor unit 420 may slide relative to the headset body 410. A bearing such as a ball or a roller joint may be provided between the headset body 410 and the sensor unit 420. The sensor unit 420 may slide relative to the headset body 410 according to a rotation of the bearing. Since the sensor unit 420 slides, a transverse movement is actually performed rather than a longitudinal movement.

In the present embodiment, the connection unit 430 may include a first receiving part 432 fixed to the headset body 410, and a second receiving part 436 fixed to the sensor housing 422, which slides relative to the first receiving part 432. A guide projection may be formed on an inner surface of the first receiving part 432. A guide groove corresponding to the guide projection is may be formed on an outer surface of the second receiving part 436. Accordingly, the first receiving part 432 and second receiving part 436 may enable the headset body 410 and the sensor unit 420 to slide relative to each other, for example.

Also, a bearing 434 configured as a ball or a roller joint may be provided between the first receiving part 432 and second receiving part 436. The bearing 434 may be in rolling contact between the first receiving part 432 and second receiving part 436, and may enable the sensor unit 420 to easily slide.

The sensor unit 420 may rotate right and left in relation to the headset body 410, such that the sensor unit 420 may continue to make stable contact with a human body through the free sliding of the connecting part 430 corresponding to a movement of the headset body 410.

When a user is working out, most displacements between the headset body 410 and the sensor unit 420 occur widthwise. Further, a movement of a longitudinal component in the headset device may not greatly affect a measurement. Although there is no longitudinal movement, a satisfactory measurement may be obtained.

Figure 10:
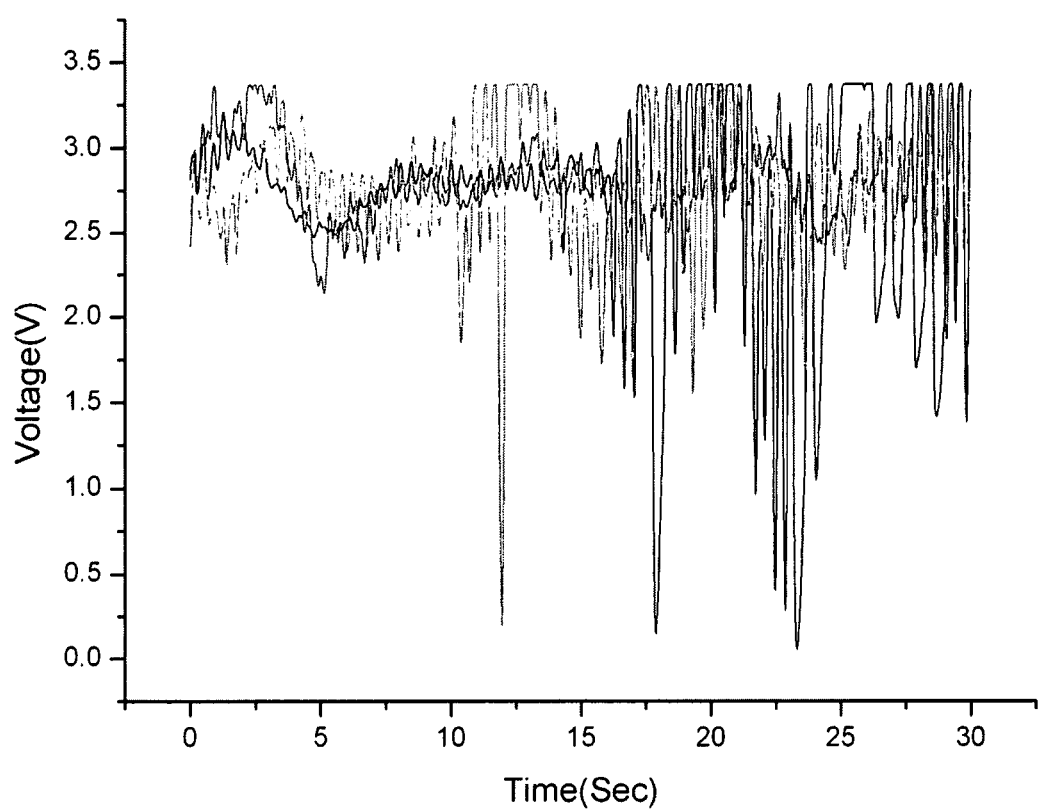
FIG. 10 illustrates performance of an integral headset device, according to one or more embodiments of the present invention.
Figure 11:
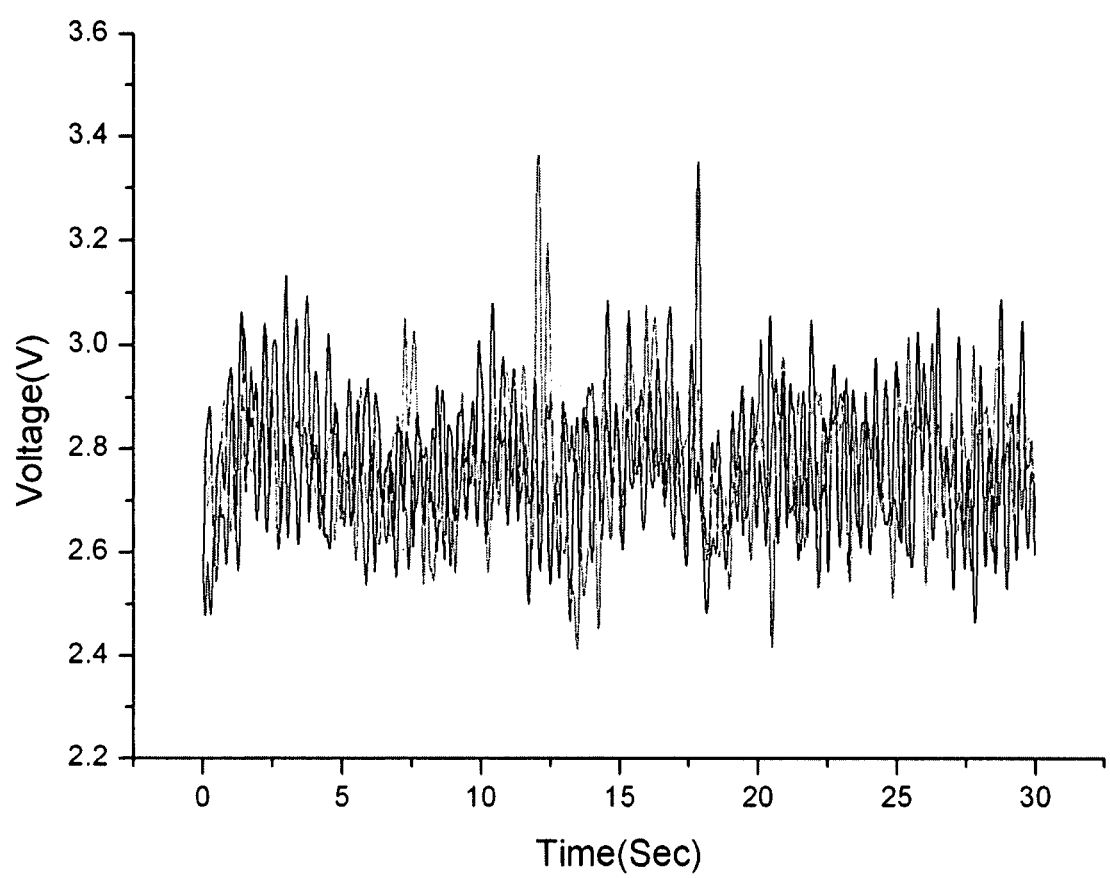
FIG. 11 illustrates performance of the headset, such as is illustrated in FIGS. 6 and 7, according to one or more embodiments of the present invention.

FIG. 10 illustrates performance of an integrated headset device. FIG. 11 illustrates performance of a headset, such as that illustrated in FIGS. 6 and 7. Namely, FIG. 10 illustrates an integrated headset, having a headset body fixed to a sensor unit. FIG. 11 illustrates a separate headset device, having a headset body separated from a sensor unit.

As illustrated in FIG. 10, a change in amplitudes of measured PPG signals is large, and a range of the change is wide. This may indicate that a PPG signal is highly influenced by user movement, and may indicate difficulty in predicting a change of amplitude while a user is working out. Accordingly, since an exercise-induced variable may not be predicted, an integral headset device may not have suitable influence on development of an algorithm.

As illustrated in FIG. 11, the change in amplitudes of measured PPG signals is relatively small, and the range of the change is improved. This indicates distortion caused by movement is overcome to some extent. Further, it indicates a change of the amplitude may be predicted while a user works out. Accordingly, a development of a stable algorithm may be possible.

According to one or more embodiments of the present invention, a headset device enables a user to stably measure a biosignal with the headset device on, and may minimize distortion caused by movement.

According to one or more embodiments of the present invention, a headset device is capable of offsetting forces caused by movement of the user during exercise, thereby providing a more gradual change in amplitudes in a dynamic environment.

According to one or more embodiments of the present invention, a headset may fix a sensor unit to a human body using a double structure, which separates a headset body from the sensor unit while a user is exercising. In addition, the accuracy of a signal detected using a photosensor or other type of sensor may be improved.

According to one or more embodiments of the present invention, a headset device is capable of exerting a constant pressure conforming to the body shape of a user, and thereby may effectively adapt to different figures. Thus, a confining feeling may be alleviated by the double structure. Accordingly, the user may wear the headset device for a long time while working out without experiencing discomfort.

Further, in addition to the above, features described above are not limited to a headset device, and may be applicable to any type of biosignal measurement devices.

Although a few embodiments of the present invention have been shown and described, the present invention is not limited to the described embodiments. Instead, it would be appreciated by those skilled in the art that changes may be made to these exemplary embodiments without departing from the principles and spirit of the invention, the scope of which is defined by the claims and their equivalents.

What is claimed is:

1. A headset device measuring a biosignal, the headset device comprising:
    a headset body including a generally arch-shaped head holder having one or more speakers installed at each end of the head holder;
    a connection unit configured to move relative to the headset body; and
    a sensor unit mounted to the connection unit to make contact with a surface of a human body, wherein:
    the connection unit includes a spring which longitudinal axis is substantially perpendicular to the surface of the human body, each end of the spring being supported by the headset body and the sensor unit respectively,
    deformation of the spring allows the headset body and the sensor unit to move relative to each other in a transverse direction,
    the connection unit is spaced apart from the sensor unit,
    the connection unit further includes a guide bar passing through the spring and connected to an end of the sensor unit, thereby inducing deformation of the spring,
    the connection unit includes a hole passing through an end of the guide bar, thereby preventing the sensor unit from separating from the connection unit
    the sensor unit includes a light emitting element and a light receiving element configured to sense a biosignal,
    the biosignal is measured by comparing features of light sensed by the light receiving element via a portion of the human body exposed to light generated by the light emitting element, and
    the light emitting element and the light receiving element are oriented in a same direction to measure a reflected light from the portion of the human body.

2. The headset device of claim 1, wherein the connection unit is configured to move such that the sensor unit moves substantially perpendicular to the surface of the human body.

3. The headset device of claim 2, wherein the connection unit comprises a joint that is combined with the headset body.

4. The headset device of claim 2, wherein the spring provides dynamic stability along a longitudinal axis thereof, which is also an axis of compression thereof, whereby the sensor unit is forced by the spring to remain in contact with the surface of the human body even during periods of activity by the user.

5. The headset device of claim 2, wherein the sensor unit comprises at least one of an amplifier configured to process the biosignal, an acceleration sensor, and a data transceiver.

6. A headset device configured to be worn on a user's head, the headset device comprising:
    a headset body including a generally arch-shaped head holder having one or more speakers at each end of the head holder;
    a connection unit including a sensor receiving part integrally connected with the headset body, and a spring in the sensor receiving part and having a longitudinal axis that is substantially perpendicular to a surface of the user's head; and
    a sensor unit including a sensor housing elastically supported by the spring to make contact with the surface of the user's head, and a photosensor in the sensor housing configured to measure a biosignal, wherein each end of the spring is supported by the headset body and the sensor unit respectively, wherein:
    deformation of the spring enables the headset body and the sensor unit to move relative to each other in a transverse direction,
    the sensor receiving part is spaced apart from the sensor housing,
    a guide bar extending from a top surface of the sensor housing toward an inner surface of the sensor receiving part through a center of the spring, and the guide bar is configured to move in the sensor receiving part, thereby inducing deformation of the spring,
    a hole is in the sensor receiving part through the end of the guide bar, thereby preventing the sensor housing from separating from the sensor receiving part;
    the photosensor includes a light emitting element and a light receiving element configured to sense a biosignal,
    the biosignal is measured by comparing features of light sensed by the light receiving element via a portion of the surface of the user's head exposed to light generated by the light emitting element, and
    the light emitting element and the light receiving element are oriented in a same direction to measure a reflected light from the portion of the surface of the user's head.

7. The headset device of claim 6, wherein the sensor unit comprises at least one of an amplifier configured to process a biosignal, an acceleration sensor, and a data transceiver.

8. A headset device comprising:
    a headset body including a generally arch-shaped head holder having one or more speakers at each end of the head holder;
    a connection unit including a first receiving part fixed to the headset body, a second receiving part engaged with the first receiving part to slide relative to the first receiving part, and at least one bearing maintaining a rolling contact between the first receiving part and the second receiving part;
    a sensor unit configured to make contact with a human body surface, the sensor unit including a sensor housing integrally connected with the second receiving part; and
    a photosensor in the sensor housing and configured to measure a biosignal, wherein:
    rotation of the bearing enables the headset body and the sensor unit to move relative to each other in a transverse direction,
    a guide projection is in one of the first receiving part and the second receiving part, and a guide groove configured to receive the guide projection is in the other of the first receiving part and the second receiving part;
    the photosensor includes a light emitting element and a light receiving element configured to sense a biosignal,
    the biosignal is measured by comparing features of light sensed by the light receiving element via a portion of the human body surface exposed to light generated by the light emitting element, and
    the light emitting element and the light receiving element are oriented in a same direction to measure a reflected light from the portion of the human body surface.

9. The headset device of claim 8, wherein the sensor unit comprises at least one of an amplifier configured to process the biosignal measured from the photosensor, an acceleration sensor, and a data transceiver.

10. A method of measuring a biosignal by wearing a headset device comprising a headset body and a sensor unit installed in the headset body, whereby the sensor unit is attached to a target portion of a human body, the method comprising:
 offsetting a movement which is transferred from the headset body to the sensor unit using a connection unit interposed between the headset body and the sensor unit, wherein the connection unit includes a spring which longitudinal axis is substantially perpendicular to the surface of the human body, with each end of the spring being connected to the headset body and the sensor unit respectively, and wherein a guide bar passes through a hole in a housing of the connection unit and passes longitudinally through the spring to connect to the sensor unit, thereby preventing the sensor unit from separating from the connection unit, while the guide bar rotates in the hole, deformation of the spring is induced such as to enable the headset body and the sensor unit to move relative to each other in a transverse direction; and
 monitoring a biosignal of the human body obtained by the sensor unit, wherein:
 the guide bar extends from a top surface of the sensor unit through the hole to an outside portion of the sensor unit,
 a size of the hole is smaller than a size of an end of the guide bar exposed from the connection unit;
 the sensor unit includes a light emitting element and a light receiving element, and the monitoring of the biosignal includes comparing features of light sensed by the light receiving element via a portion of the human body exposed to light generated by the light emitting element, and
 the light emitting element and the light receiving element are oriented in a same direction to measure a reflected light from the portion of the human body.

11. The method of claim 10, wherein the connection unit moves such that the sensor unit moves substantially perpendicular to the surface of the human body.

12. The method of claim 11, wherein the connection unit comprises a joint which is combined with the headset body and the sensor unit.

13. The method of claim 11, wherein the spring provides dynamic stability along a longitudinal axis thereof, which is also an axis of compression thereof, whereby the sensor unit elastically moves relative to the headset body and is urged by the spring to remain in contact with the surface of the human body even during periods of activity by the user.

14. A measurement device for measuring a biosignal comprising:
 a body wearable on a human head, the body including a generally arch-shaped head holder having one or more speakers installed at each end of the head holder;
 a connection unit configured to move relative to the body in a transverse direction; and
 a sensor unit mounted to the connection unit and configured to make contact with a surface of the human head, wherein the connection unit is configured to restrict a movement of the sensor unit to move substantially perpendicular to the surface of the human head, wherein the connection unit includes a spring, each end of which being supported by the body and the sensor unit respectively to restrict the movement of the sensor unit, wherein:
 the connection unit is spaced apart from the sensor unit,
 the connection unit includes a guide bar passing through a center of the spring, and the guide bar is configured to move in the connection unit, thereby inducing deformation of the spring,
 the connection unit includes a hole through the end of the guide bar, thereby preventing the sensor unit from separating from the connection unit;
 the sensor unit includes a light emitting element and a light receiving element configured to sense a biosignal,
 the biosignal is measured by comparing features of light sensed by the light receiving element via a portion of the surface of the human head exposed to light generated by the light emitting element, and
 the light emitting element and the light receiving element are oriented in a same direction to measure a reflected light from the portion of the human head.

* * * * *